United States Patent
Cheng et al.

(10) Patent No.: US 9,775,885 B2
(45) Date of Patent: Oct. 3, 2017

(54) TMD1 PROTEIN FOR TREATING BONE LOSS DISEASES

(71) Applicant: KAOHSIUNG MEDICAL UNIVERSITY, Kaohsiung (TW)

(72) Inventors: Tsung-Lin Cheng, Kaohsiung (TW); Jwu-Lai Yeh, Kaohsiung (TW); Mei-Ling Ho, Kaohsiung (TW); Guey-Yueh Shi, Tainan (TW); Hua-Lin Wu, Tainan (TW)

(73) Assignee: KAOHSIUNG MEDICAL UNIVERISTY, Kaohsiung (TW)

( * ) Notice: Subject to any disclaimer, the term of this patent is extended or adjusted under 35 U.S.C. 154(b) by 0 days.

(21) Appl. No.: 15/415,806

(22) Filed: Jan. 25, 2017

(65) Prior Publication Data
US 2017/0216407 A1    Aug. 3, 2017

Related U.S. Application Data

(60) Provisional application No. 62/288,430, filed on Jan. 29, 2016.

(51) Int. Cl.
*A61K 38/00* (2006.01)
*A61P 19/08* (2006.01)
*A61K 38/36* (2006.01)

(52) U.S. Cl.
CPC .................................. *A61K 38/366* (2013.01)

(58) Field of Classification Search
None
See application file for complete search history.

(56) References Cited

U.S. PATENT DOCUMENTS

| | | | |
|---|---|---|---|
| 7,341,992 B2 * | 3/2008 | Conway | C07K 14/7455 514/12.2 |
| 2005/0147611 A1 * | 7/2005 | Boyle | C07K 14/70578 424/145.1 |
| 2010/0113568 A1 * | 5/2010 | Wu | A61K 38/366 514/44 R |

OTHER PUBLICATIONS

Li et al. The role of thrombomodulin lectin-like domain in inflammation. J Biomed Sci, 2012. vol. 19, No. 34, pp. 1-8.*

* cited by examiner

*Primary Examiner* — Marcela M Cordero Garcia
(74) *Attorney, Agent, or Firm* — Hannah M. Tien

(57) ABSTRACT

The present invention relates to a method for treating a bone loss disease, condition, or disorder in a subject in need thereof, comprising administering to said subject a pharmaceutically effective amount of a composition comprising thrombomodulin lectin-like domain (TMD1).

6 Claims, 7 Drawing Sheets
(4 of 7 Drawing Sheet(s) Filed in Color)

TMD1 PROTEIN FOR TREATING BONE LOSS DISEASES

The present application claims priority to U.S. Provisional Appl. No. 62/288,430, filed Dec. 29, 2016, incorporated herein by reference in its entirety.

FIELD OF THE INVENTION

The present invention relates to a method for treating bone loss diseases by inhibiting receptor activator of nuclear factor-κB ligand (RANKL)-induced osteoclast differentiation.

BACKGROUND OF THE INVENTION

Bone is a living organ that is continuously being reshaped in a process called remodeling. In this process, cells called osteoclasts resorb bone tissues whereas cells called osteoblasts deposit new bone tissue. Osteoblasts can become trapped within the bone matrix they secrete, promoting their differentiation into osteocytes. These cells are thought to play an important role in sensing bone load. Under high loading conditions, osteoblasts increase bone mass, whereas under low loading conditions, osteoclasts remove bone tissue, optimizing its structure. Therefore, osteoclasts are closely related to bone loss or decreased bone density.

People may have bone loss or decreased bone density due to physiological factors or other external factors, which leads to osteoporosis. The signs of osteoporosis may include fracture, back pain, limited ability to act (even unable to move). Currently the treatment methods for osteoporosis include nutrition improvement, exercise, medication, etc. Regarding medication, drugs for clinical use comprise: estrogen or estrogen analogues, drugs for treatment of osteoporosis induced by glucocorticoid hormones, diphosphate, or calcitonin, etc. However, all these drugs described above have side effects, for example, diphosphate may cause nausea, indigestion, diarrhea, or constipation, and calcitonin may cause facial flushing, frequent urination, nausea, or itchy skin. Most of all, the drugs described above are unable to suppress the generation of osteoclasts cells, thus are unable to effectively cure osteoporosis.

Receptor activator of nuclear factor-κB ligand (RANKL) is a critical factor to induce the differentiation of osteoclasts from bone marrow-derived macrophages (BMM).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

The present invention relates to a method for treating a bone loss disease, condition, or disorder in a subject in need thereof, comprising administering to said subject a pharmaceutically effective amount of a composition comprising thrombomodulin lectin-like domain (TMD1).

DETAILED DESCRIPTION OF THE INVENTION

The object of the present invention is to treat a disease, condition, or disorder associated with bone loss. In the present invention, receptor activator of nuclear factor-κB ligand (RANKL)-induced osteoclast differentiation is inhibited to achieve therapeutic effect of osteoporosis. The thrombomodulin (TM) used in the present invention is a naturally occurring enzyme. The thrombomodulin lectin-like domain (the first domain of TM, TMD1) can be formulated into a protein drug for inhibiting activation of RANKL, thereby achieve treatment of osteoporosis by inhibition of osteoclast differentiation.

Figure 7:
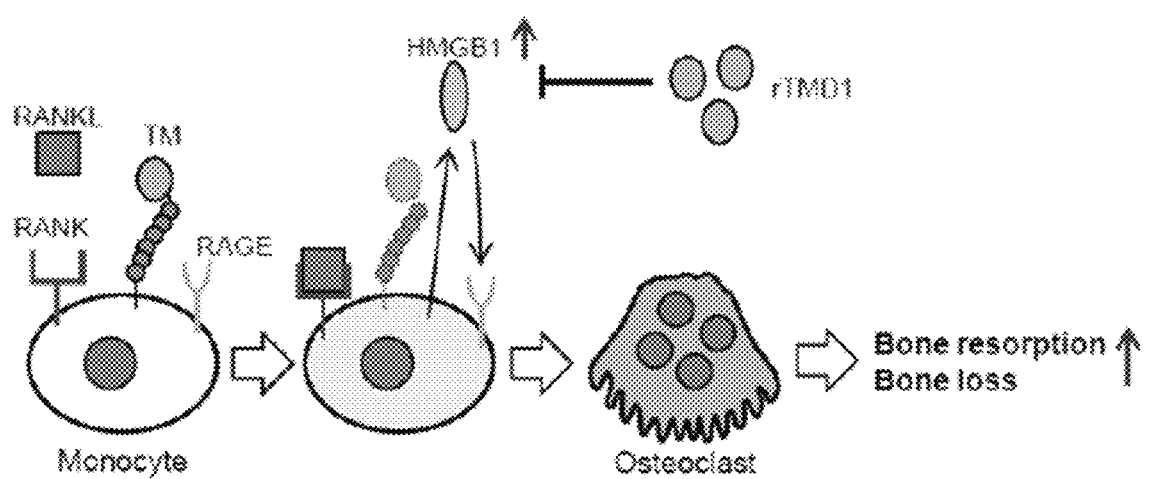
FIG. 7 shows a schematic model of TM in osteoclastogenesis. During osteoclastogenesis, RANKL reduces TM expression and promotes extracellular HMGB1 secretion in monocytes, which results in the enhancement of bone resorption and bone loss. In addition, rTMD1 treatment can inhibit HMGB1 secretion, bone resorption, and bone loss.

Using the model of RANKL-induced osteoclast differentiation in RAW264.7 cells, the present invention shows for the first time that supplementation of TMD1 significantly attenuates the osteoclast differentiation and bone resorption in a dose-dependent manner. In summary, as shown in the illustrated model in FIG. 7, the present invention demonstrates that TM expressed by monocytes/macrophages is a negative regulator of osteoclastogenesis, and treatment of rTMD1 can inhibit OVX-induced bone loss. These observations provide a new therapeutic strategy for bone loss disorders. Thus, TMD1 may be a new therapeutic treatment for bone loss diseases.

Therefore, the present invention provides a method for treating a bone loss disease, condition, or disorder in a subject in need thereof, comprising administering to said subject a pharmaceutically effective amount of a composition comprising thrombomodulin lectin-like domain (TMD1).

In an embodiment, the method inhibits osteoclast differentiation in the subject.

In a further embodiment, the method inhibits activation of receptor activator of nuclear factor-κB ligand (RANKL) in the subject.

In an embodiment, the bone loss disease, condition, or disorder includes but not limited to osteoporosis or rheumatoid arthritis.

In an embodiment, the subject is a mammal. In a further embodiment, the subject is a human.

EXAMPLES

The examples below are non-limiting and are merely representative of various aspects and features of the present invention. Therefore, the method of the present invention should not be limited to only for diagnosing neurodegenerative disease.

Example 1

Methods and Materials
Experimental Animals

LysMcre/TM$^{flox/flox}$ mice with myeloid specific TM deletion were generated as previously reported. Compared with their controls (TM$^{flox/flox}$ mice), TM expression in the myeloid linage (macrophages and neutrophils), but not in other tissues and organs, was suppressed in LysMcre/TM$^{flox/flox}$ mice. Mice lacking the lectin-like domain of TM (TM$^{LeD/LeD}$ mice) and their controls (TM$^{WT/LeD}$ mice) were a gift from Dr. Conway. These B6-background mice were maintained in a pathogen-free animal facility at the Center of the National Cheng Kung University (NCKU). All animal protocols were approved by the Animal Care Committee of NCKU. Bilateral ovariectomy (OVX), as described previously, was performed at 8 weeks of age.

Cell Isolation

Human PBMCs were separated from whole blood using a Ficoll-Paque PLUS (GE Healthcare, Brussels, Belgium) gradient based on the manufacturer's instructions. Mouse bone marrow macrophages/monocytes (BMMs) were isolated from the femur and tibia (6 to 12 weeks old) as described previously with some modifications. Briefly, isolated total bone marrow cells were incubated overnight in complete Minimum Essential Medium (Alpha modification; α-MEM). Then, nonadherent cells were collected and mononuclear cells were prepared using a Ficoll-Hypaque (GE Healthcare, Piscataway, N.J., USA) density gradient centrifugation. The BMMs were evenly scattered across the interface between Ficoll-Hypaque and medium.

Osteoclast Culture and TRAP Staining

Cells (RAW264.7, PBMCs, or BMMs) were cultured in 96-well plates ($1 \times 10^5$ cells/well). RANKL and M-CSF were added to stimulate osteoclast generation. Media were replenished every 2 days. On day 8, cells were fixed with 3% formaldehyde and were stained with tartrate acid phosphatase (TRAP) (Sigma, St. Louis, Mo., USA). TRAP-positive cells with three or more nuclei were counted as osteoclasts.

TRAP Activity Assay

TRAP activity was measured using 4-NPP as substrate, based on the microplate assay method with modifications. A 50 μL sample was incubated with 150 μL of substrate consisting of 8 mM 4-NPP in 100 mM sodium acetate buffer containing 500 mM sodium tartrate at 37° C. for 40 min with pH 5.0. The reaction was terminated by the addition of 50 μL 3 M NaOH. Absorbance was measured at 405 nm in a microplate reader (SPECTRAmax™ 340; Molecular Devices, Palo Alto, Calif., USA).

Western Blot Analysis

Cells were lysed and western blot analysis was performed as previously described. Approximately 50 μg of total protein was separated in a 10% sodium dodecyl sulfate-polyacrylamide gel and was transferred onto a polyvinylidene difluoride membrane. After probing with a primary and a secondary antibody, the signal was detected using an enhanced chemiluminescence reagent (Amersham Pharmacia Biotech).

Bone Resorption Assay

Bone resorption activities were determined by the bone resorption assay kit (Cosmo Bio. Co. Ltd., Tokyo, Japan) based on the manufacturer's instructions. In brief, RAW264.7 cells were incubated on fluoresceinated calcium phosphate-coated plates with M-CSF (30 ng/ml) and RANKL (30 ng/ml) in the presence or absence of various concentrations of rTMD1 for 7 days. The RANKL-induced bone resorption activity was evaluated by measuring the fluorescence intensity of the conditioned medium with an excitation wavelength of 485 nm and an emission wavelength of 535 nm.

Micro-Computed Tomography (μCT)

All μCT analyses were consistent with the current guidelines. 29 Bone samples from all groups were imaged using a SkyScan-1076 Micro-CT System (Skyscan, Belgium). For trabecular bone analysis, the μCT scanner was operated at 45 kV, 220 μA, 0.4μ rotation step, 0.5 mm aluminum filter, and a scan resolution of 18 pin/pixel. The following parameters were measured: total bone volume (TV, mm3), trabecular bone volume (BV, mm3), and trabecular bone volume fraction (BV/TV, %).

Results

Figure 1:
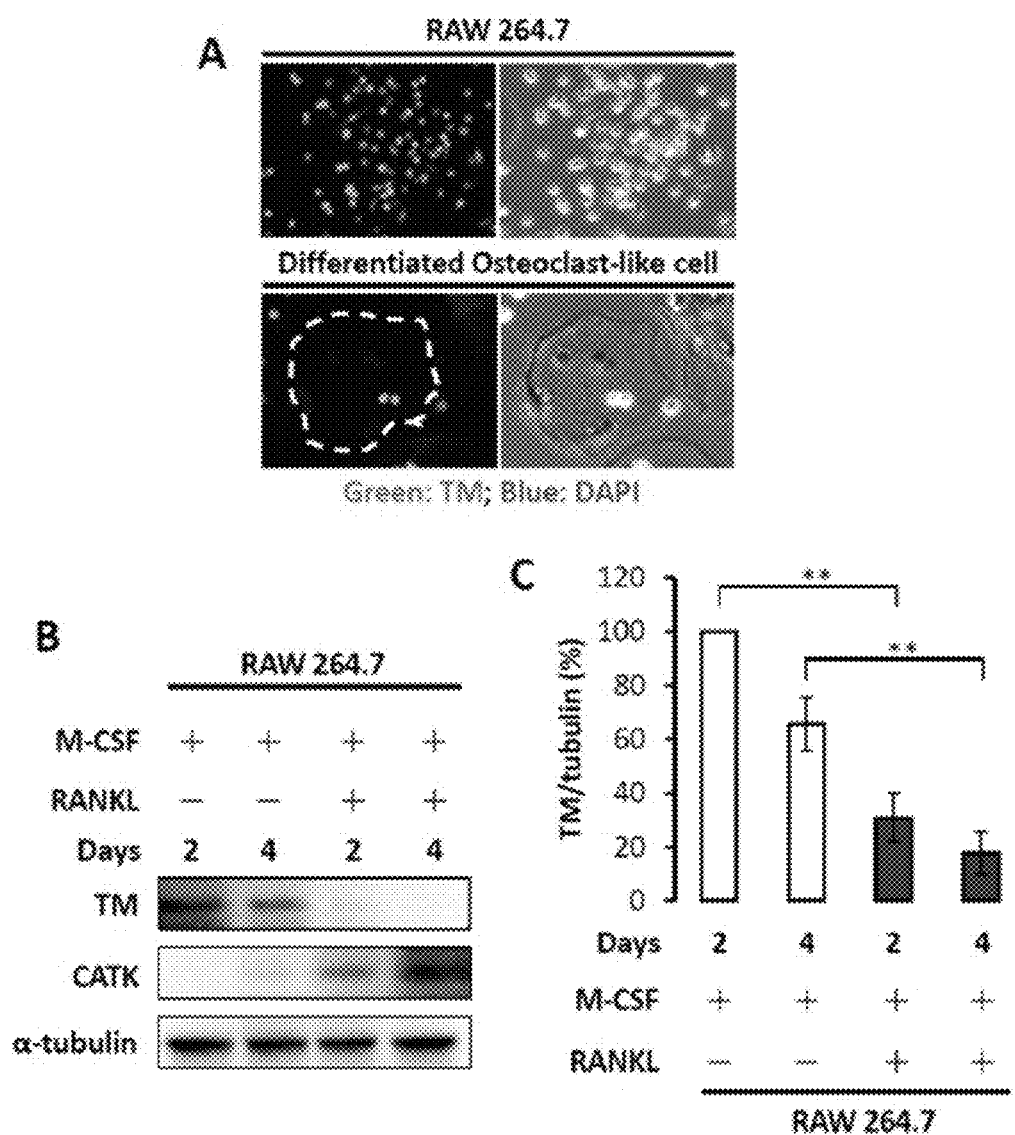
FIG. 1 shows down-regulated TM expression in RAW 264.7-differentiated osteoclasts. A. TM protein expression detected using IF staining in RAW 264.7 cells and differentiated osteoclast-like cells treated with M-CSF (20 ng/ml) and RANKL (30 ng/ml) for 4 days (original magnification ×200). B. Western blot analysis of TM and CATK expression in RAW 264.7 cells treated with M-CSF and RANKL. Representative figures from three independent experiments are shown. C. Quantitative representation of (B). $P<0.01$
Figure 2:
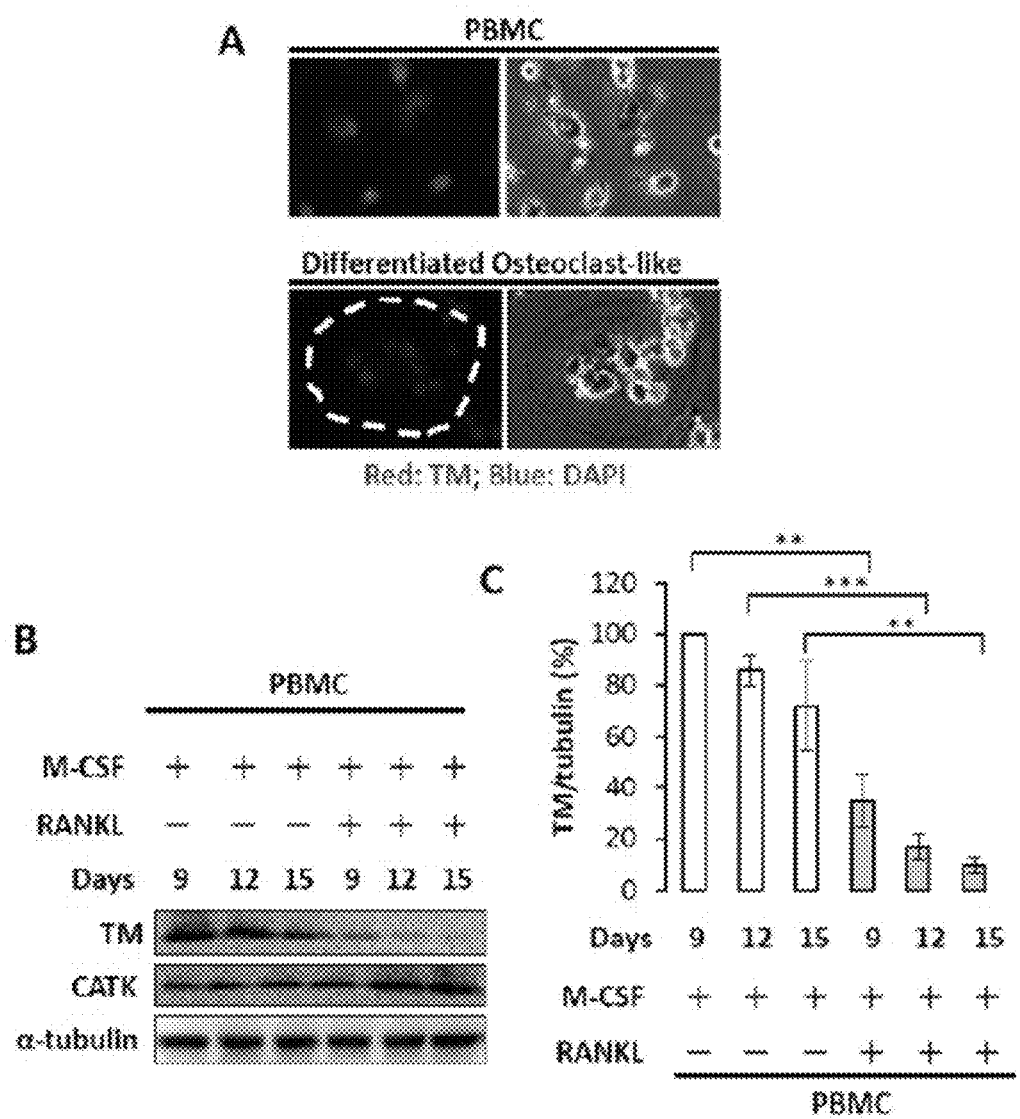
FIG. 2 shows down-regulated TM expression in PBMC-differentiated osteoclasts. A. TM protein expression detected using IF staining in PBMCs and differentiated osteoclast-like cells treated with M-CSF (20 ng/ml) and RANKL (30 ng/ml) for 1 week (original magnification ×200). B. Western blot analysis of TM and CATK expression in PBMCs treated with M-CSF and RANKL. Representative figures from three independent experiments are shown. C. Quantitative representation of (B). $P<0.01$, ***$P<0.001$.

Decreased TM Protein Expression in Monocytes/Macrophages During Osteoclastogenesis Osteoclastogenesis in mouse RAW 264.7 cells and human PBMCs was induced using RANKL and M-CSF to evaluate the levels of TM protein during the process. Immunofluorescence staining revealed TM expression dramatically decreased as RAW 264.7 cells differentiated into osteoclast-like cells (FIG. 1A). Western blot analysis showed that treatment of RAW 264.7 cells with RANKL reduced TM and increased CATK, a marker of osteoclasts, in a time-dependent manner (FIG. 1, (B)-(C)). Similar results were observed in human PBMCs (FIG. 2). Collectively, these results suggest that TM expression in monocytes/macrophages may be inversely related to osteoclastogenesis.

Figure 3:
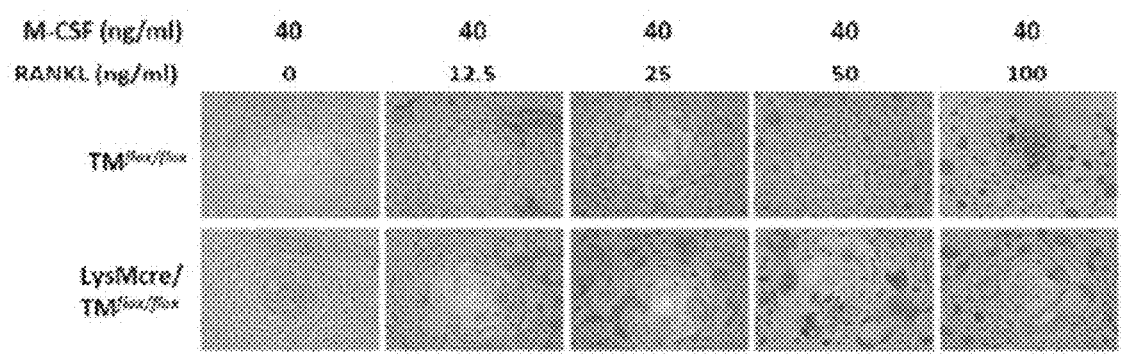
FIG. 3 shows that myeloid-specific deletion of TM enhances osteoclasts formation. A. TRAP staining analysis in osteoclasts differentiated from primary cultured macrophages obtained from $TM^{flox/flox}$ and $LysMcre/TM^{flox/flox}$ mice with treatment of M-CSF and various concentrations of RANKL for differentiation (original magnification ×200). B. Quantitation of TRAP positive multi-nucleated osteoclasts (MNCs) per well. ***$P<0.001$. Experiments were repeated three times.
Figure 3:
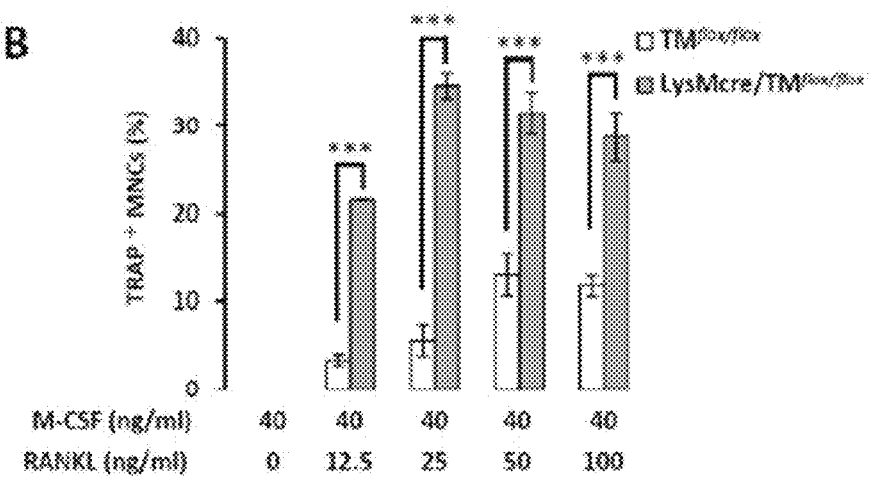

Deficiency of Full-Length TM in Macrophages Enhances the RANKL-Induced Osteoclastogenesis To investigate whether TM might be a negative regulator in osteoclastogenesis, macrophages from myeloid-specific transgenic mice were isolated. TRAP staining analysis showed that RANKL can dose-dependently induce osteoclastogenesis in macrophages from LysMcre/TM$^{flox/flox}$ and TM$^{flox/flox}$ mice. However, the cell areas in the LysMere/TM$^{flox/flox}$ mice were larger than those from TM$^{flox/flox}$ mice (FIG. 3, (A)). Quantification of the results showed that the ratio of differentiated TRAP positive multinucleated cells (TRAP+ MNC) in the LysMere/TM$^{flox/flox}$ group was at least 3-fold higher compared with that in the TM$^{flox/flox}$ group (FIG. 3, (B)). These results indicate that the existence of full-length TM in macrophages may hinder RANKL-induced osteoclastogenesis.

TM Lectin-Like Domain in Macrophages Retards RANKL-Induced Osteoclastogenesis

Figure 4:
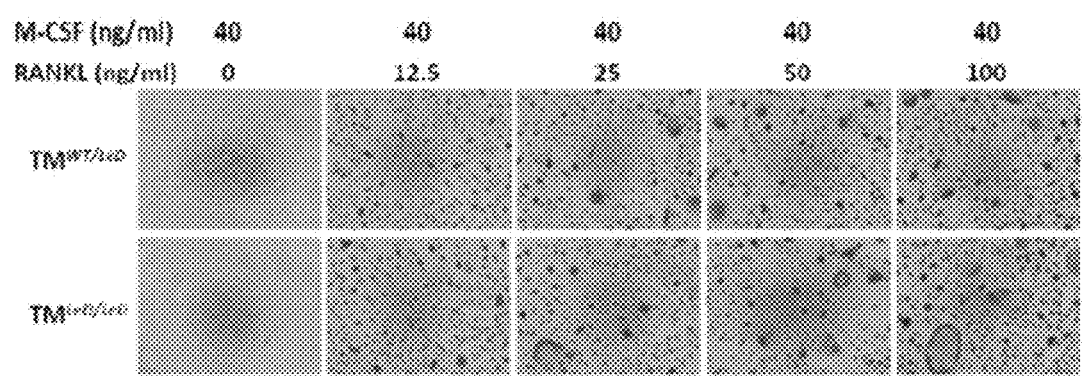
FIG. 4 shows that TM lectin-like domain on macrophages retards RANKL-induced osteoclast formation. A. TRAP staining of osteoclasts differentiated from primary cultured macrophages obtained from $TM^{WT/LeD}$ and $TM^{LeD/LeD}$ mice with treatment of M-CSF and various concentrations of RANKL for differentiation (original magnification ×200). B. Quantitation of TRAP activity using 4-NPP as substrate. *$P<0.05$, **$P<0.01$. Experiments were repeated three times.
Figure 4:
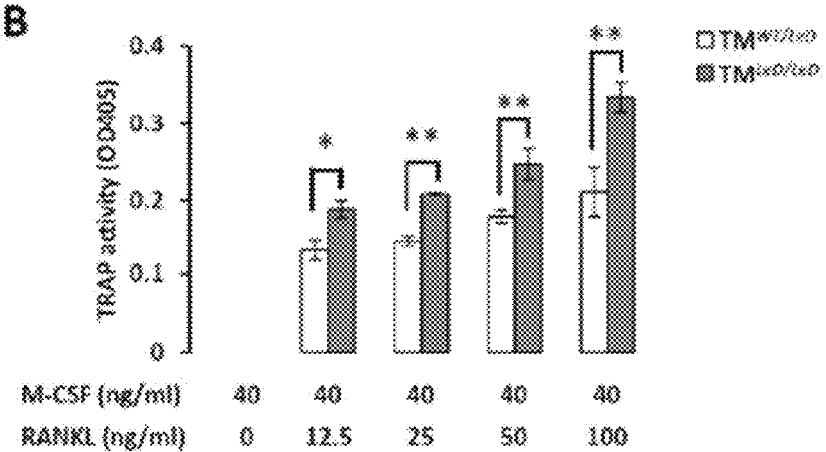

It has been shown that osteoblast-derived C-type lectin can inhibit osteoclast formation. To further investigative whether the lectin-like domain of TM might contribute to the inhibition of RANKL-induced osteoclastogenesis, primary macrophages from TM$^{WT/LeD}$ and TM$^{LeD/LeD}$ mice were examined. TRAP staining analysis showed that RANKL can induce osteoclastogenesis in primary cells from both TM$^{WT/LeD}$ and TM$^{LeD/LeD}$ mice. However, the cell area of some OCs in the TM$^{LeD/LeD}$ group appeared larger than in the TM$^{WT/LeD}$ group (FIG. 4, (A)). Moreover, the detected activities of TRAP in the TM$^{LeD/LeD}$ group were significantly higher than those in the TM$^{WT/LeD}$ group (FIG. 4, (B)). These results suggest that the lectin-like domain of TM may have a critical effect in inhibiting RANKL-induced osteoclastogenesis.

Deletion of the Full-length TM or Deletion of the TM Lectin-like Domain Enhanced Extracellular HMGB1 Production in Macrophages and Ovariectomy-induced Bone Loss.

Figure 5:
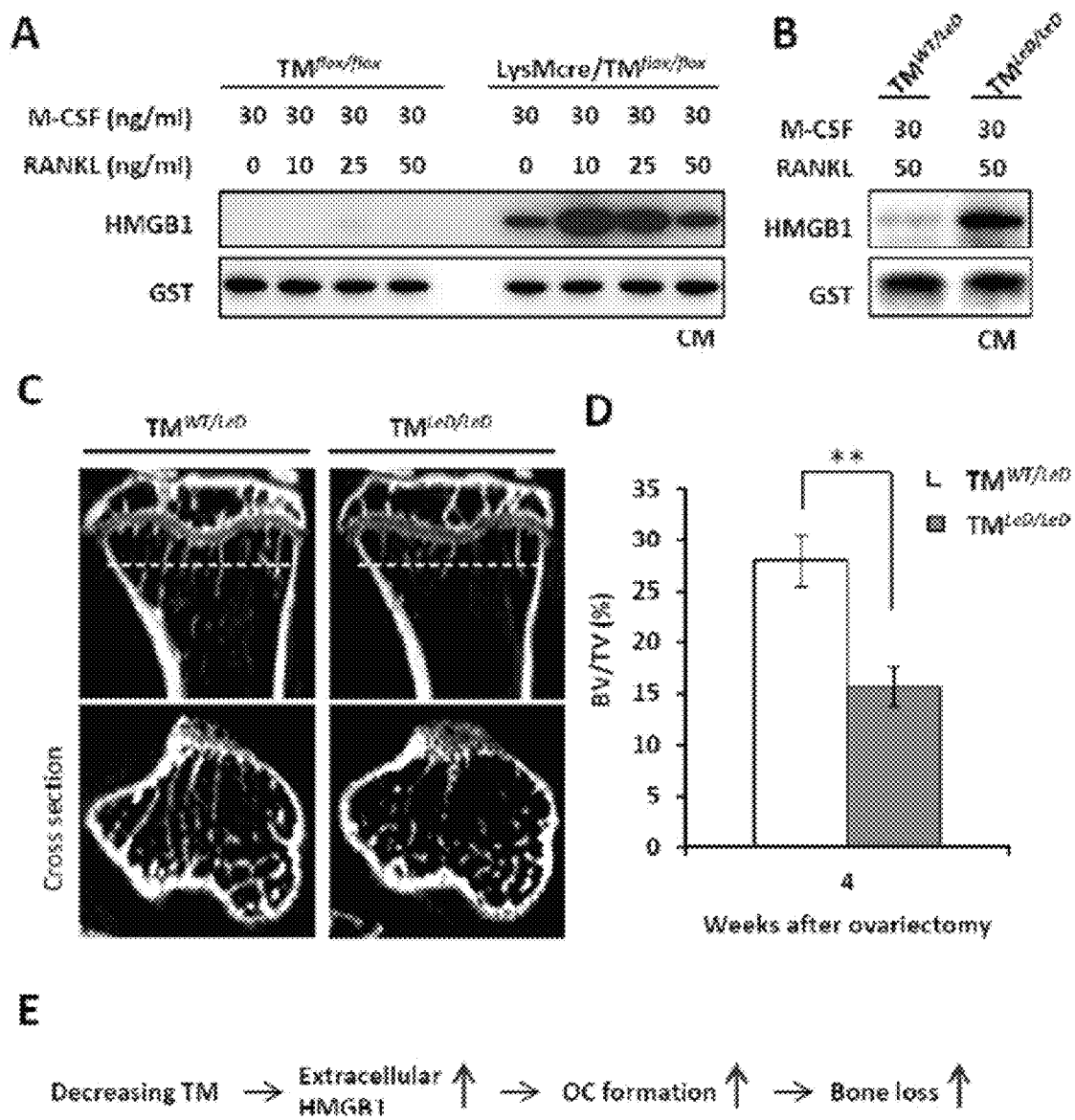
FIG. 5 shows that TM deficiency enhances the production of extracellular HMGB1 and ovariectomy-induced bone loss. Evaluation of extracellular HMGB1 production by western blot analysis in primary cultured macrophages from $TM^{flox/flox}$ and $LysMere/TM^{flox/flox}$ mice A., and from $TM^{WT/LeD}$ and $Tm^{LeD/LeD}$ mice B. Glutathionine-S-transferase (GST) was used as an internal control. CM: conditioned medium. Representative figures from three independent experiments are shown. C. Bone loss in tibia was detected by μCT scanning after 4 weeks of ovariectomy. Dashed lines indicate the cross sections. D. Quantitative results of trabecular bone volume fraction (BV/TV). BV, trabecular bone volume; TV, total bone volume. **$P<0.01$. n=5. E. Potential mechanisms of TM deficiency in promotion of bone loss.

Since the release of HMGB1 was required for RANKL-induced osteoclastogenesis, the effects of TM deficiency on the production of extracellular HMGB1 were further evaluated. As shown in FIG. 5, HMGB1 protein production in the conditioned medium from RANKL-treated LysMere/TM$^{flox/flox}$ cells was substantially higher than that from TM$^{flox/flox}$ cells (FIG. 5, (A)). Likewise, the extracellular HMGB1 produced by TM$^{LeD/LeD}$ macrophages was also higher than that from TM$^{WT/LeD}$ (FIG. 5, (B)). In addition, μCT scanning showed that tibia bone loss induced by ovariectomy was significantly more severe in TM$^{LeD/LeD}$ mice than in TM$^{WT/LeD}$ mice (FIG. 5, (C)-(D)). These data suggested that TM deficiency in macrophages, likely in association with production of extracellular HMGB1, enhanced osteoclast formation and bone loss (FIG. 5, (E)).

Treatment with rTMD1 Inhibits Bone Resorption and Bone Loss

Figure 6:
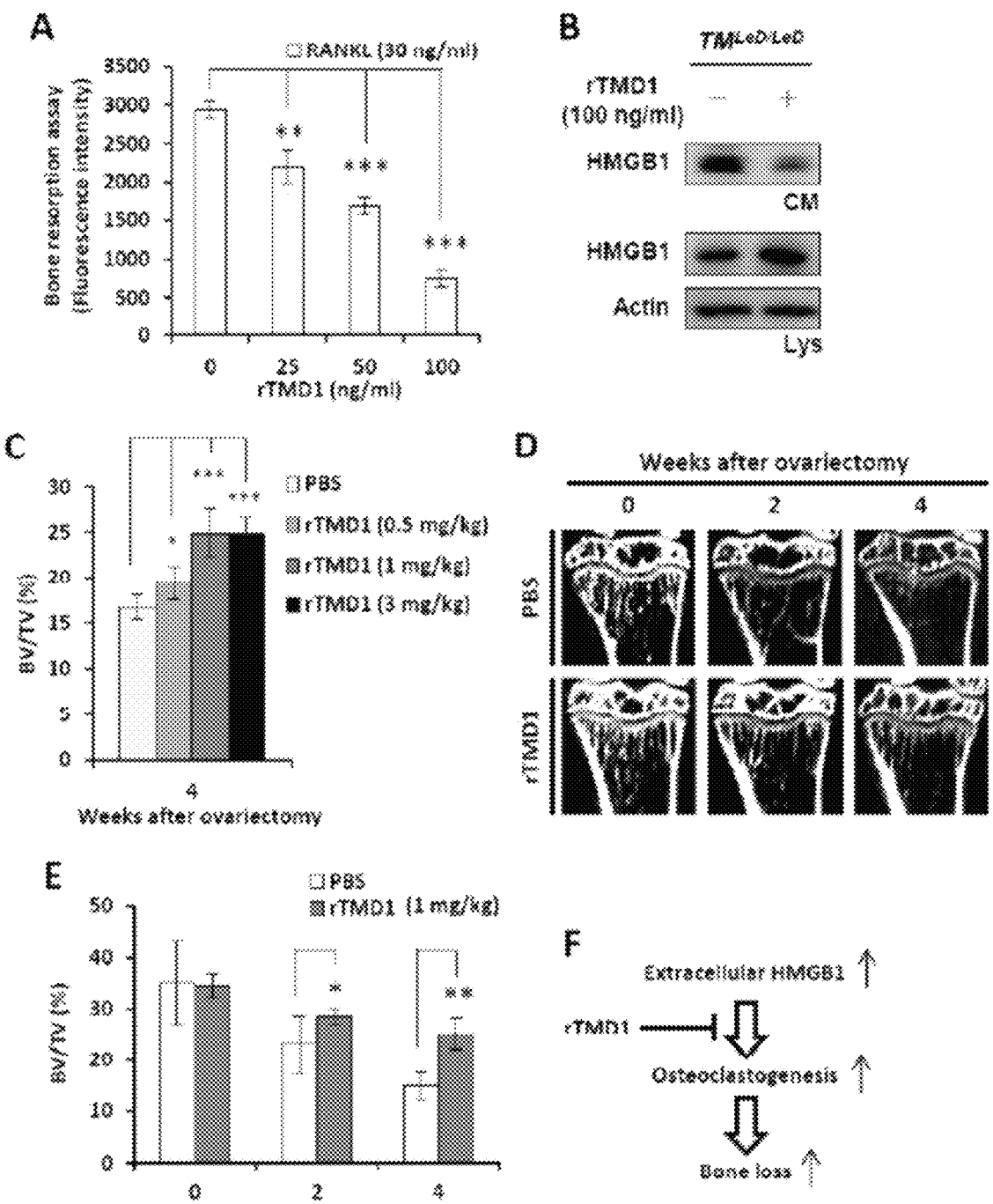
FIG. 6 shows that recombinant TM lectin-like domain (rTMD1) suppresses RANKL-induced bone resorption and reduces ovariectomy-induced bone loss. A. Results of bone resorption assay in RAW264.7 cells treated with RANKL and rTMD1. Experiments were repeated three times. B. Production of extracellular HMGB1 in bone marrow macrophages/monocytes from $TM^{LeD/LeD}$ mice in response to rTMD1 treatment. CM, conditioned medium. Lys, cell lysates. C. Quantitative results of bone volume fraction (BV/TV) in ovariectomized wild-type mice treated with various doses of intraperitoneal rTMD1 injection. BV, trabecular bone volume; TV, total bone volume. n=5. D. Bone loss in tibia was detected by μCT scanning in wild-type mice with and without rTMD1 treatment within 4 weeks of ovariectomy. E. Quantitative results of D. n=5. F. Proposed mechanism of rTMD1 in the reduction of ovariectomy-induced bone loss. *$P<0.05$, $P<0.01$, *$P<0.001$.

The effects of human rTMD1 on bone resorption in vitro and bone loss in vivo were investigated. Results of the bone resorption assay indicated that rTMD1 treatment inhibited RANKL-induced bone resorption in a dose-dependent manner (FIG. 6, (A)) and also decreased the production of extracellular HMGB1 in BMMs from TM$^{LeD/LeD}$ mice (FIG. 6, (B)). In addition, rTMD1 treatment dose-dependently increased the bone volume fraction (BV/TV) in ovariectomized wild-type mice (FIG. 6, (C)). Consistent with these results, rTMD1 treatment inhibited bone loss across a 4-week period (FIG. 6, (D)-(E)). These results suggest that rTMD1 inhibits bone loss, at least in part, through blockade of HMGB1-induced osteoclastogenesis (FIG. 6, (F)).

One skilled in the art readily appreciates that the present invention is well adapted to carry out the objects and obtain the ends and advantages mentioned, as well as those inherent therein. The methods and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating a bone loss disease, condition, or disorder in a subject in need thereof, comprising administering to said subject a pharmaceutically effective amount of a composition comprising thrombomodulin lectin-like domain (TMD1), provided that the bone loss disease, condition, or disorder does not comprise rheumatoid arthritis or arthritis.

2. The method of claim 1, which inhibits activation of receptor activator of nuclear factor-κB ligand (RANKL) in the subject.

3. The method of claim 1, which inhibits osteoclast differentiation in the subject.

4. The method of claim 1, wherein the bone loss disease, condition, or disorder comprises osteoporosis.

5. The method of claim 1, wherein the subject is a mammal.

6. The method of claim 1, wherein the subject is a human.

* * * * *